US009950120B2

(12) United States Patent
Morris

(10) Patent No.: US 9,950,120 B2
(45) Date of Patent: Apr. 24, 2018

(54) DISPLAY ASSEMBLY FOR A DRUG DELIVERY DEVICE

(71) Applicant: Sanofi, Paris (FR)

(72) Inventor: Anthony Paul Morris, Coventry West Midlands (GB)

(73) Assignee: Sanofi, Paris (FR)

( * ) Notice: Subject to any disclaimer, the term of this patent is extended or adjusted under 35 U.S.C. 154(b) by 371 days.

(21) Appl. No.: 14/782,676

(22) PCT Filed: Apr. 8, 2014

(86) PCT No.: PCT/EP2014/056997
§ 371 (c)(1),
(2) Date: Oct. 6, 2015

(87) PCT Pub. No.: WO2014/166915
PCT Pub. Date: Oct. 16, 2014

(65) Prior Publication Data

US 2016/0067408 A1 Mar. 10, 2016

(30) Foreign Application Priority Data

Apr. 10, 2013 (EP) .................................... 13163104

(51) Int. Cl.
*A61M 5/31* (2006.01)
*A61M 5/315* (2006.01)
*A61M 5/24* (2006.01)

(52) U.S. Cl.
CPC .......... *A61M 5/31528* (2013.01); *A61M 5/31* (2013.01); *A61M 5/31541* (2013.01);
(Continued)

(58) Field of Classification Search
CPC .. A61M 2005/3125; A61M 2005/3126; A61M 2205/583; A61M 5/31528; A61M 5/31558
See application file for complete search history.

(56) References Cited

U.S. PATENT DOCUMENTS 5,961,495 A * 10/1999 Walters ............. A61M 5/31553 604/111
6,048,336 A * 4/2000 Gabriel ................... A61M 5/24 604/207

(Continued)

FOREIGN PATENT DOCUMENTS

WO WO 2006/039930 4/2006
WO WO 2008/058665 5/2008
WO WO 2012/049143 4/2012

OTHER PUBLICATIONS

International Preliminary Report on Patentability in International Application No. PCT/EP2014/056997, dated Oct. 13, 2015, 6 pages.

(Continued)

*Primary Examiner* — Kami A Bosworth
*Assistant Examiner* — William Carpenter
(74) *Attorney, Agent, or Firm* — Fish & Richardson P.C.

(57) ABSTRACT

A display assembly for a drug delivery device (100) is provided. The display assembly comprises a housing (10) having a proximal end (17), a distal end (16) and a longitudinal axis (x). The display assembly further comprises a display member (120) defining a display member window (122), wherein the display member (120) is rotationally locked to but movable with respect to the housing (10) along the longitudinal axis (x). The display assembly further comprises an indication member (60) comprising indicia (66) and a movable member (110) which is rotationally coupled to the indication member (60). The movable member (110) is further coupled to the display member (120) and rotatable with respect to the housing (10). When the movable member (110) is rotated with respect to the housing (10), the rotating movable member (110) moves the display member (120) axially with respect to the housing (10) to display different indicia (66) through the display member window (122).

18 Claims, 8 Drawing Sheets

(52) U.S. Cl.
CPC .... *A61M 5/31551* (2013.01); *A61M 5/31558* (2013.01); *A61M 5/31565* (2013.01); *A61M 5/31561* (2013.01); *A61M 5/31585* (2013.01); *A61M 5/31593* (2013.01); *A61M 2005/2407* (2013.01); *A61M 2005/3125* (2013.01); *A61M 2005/3126* (2013.01); *A61M 2205/583* (2013.01)

(56) References Cited

U.S. PATENT DOCUMENTS

2010/0168677 A1* 7/2010 Gabriel ............. A61M 5/31551 604/189
2010/0274198 A1* 10/2010 Bechtold ........... A61M 5/31551 604/189
2013/0016105 A1* 1/2013 Raab ................. A61M 5/31551 345/440
2015/0297836 A1* 10/2015 Moller .............. A61M 5/31536 604/207
2016/0045664 A1* 2/2016 Morris .............. A61M 5/31551 604/207
2016/0051766 A1* 2/2016 Marsh ..................... A61M 5/20 604/207
2016/0051767 A1* 2/2016 Higgins ............ A61M 5/31586 604/211

OTHER PUBLICATIONS

International Search Report and Written Opinion in International Application No. PCT/EP2014/056997, dated Jul. 21, 2014, 8 pages.

* cited by examiner

DISPLAY ASSEMBLY FOR A DRUG DELIVERY DEVICE

CROSS-REFERENCE TO RELATED APPLICATIONS

The present application is a U.S. National Phase Application pursuant to 35 U.S.C. § 371 of International Application No. PCT/EP2014/056997 filed 6 Oct. 2015, which claims priority to European Patent Application No. 13163104.6 filed on 10 Apr. 2014.

The present disclosure relates to a drive assembly for a drug delivery device, e.g. an injector-type device and/or a pen-type device.

Drug delivery devices are, for example, known from WO 2008/058665 A1.

It is an object of the present disclosure to provide an assembly of one or more components which facilitate an indication of dose information by a drug delivery device and/or to provide an improved drug delivery device.

This object is achieved by the subject-matter of the independent claim. Advantageous embodiments and refinements are subject-matter of the dependent claims.

One object relates to a display assembly for a drug delivery device. The display assembly comprises a housing having a proximal end and a distal end and a longitudinal axis. A longitudinal axis may extend through the proximal end and the distal end.

The “distal end” of the drug delivery device or a component of the drug delivery device shall mean the end which is closest to the dispensing end of the drug delivery device. The “proximal end” of the drug delivery device or a component of the drug delivery device shall mean the end which is furthest away from the dispensing end of the drug delivery device. The display assembly further comprises a display member defining a display member window. The display member window is rotationally locked to but movable with respect to the housing along the longitudinal axis.

The display assembly further comprises an indication member comprising indicia. The indication member may comprise a sleeve-like shape. An outer surface of the indication member may be provided with the indicia. The indicia may provide dose information. Preferably, the indicia indicate units or quantities of drug to be dispensed from the drug delivery device, respectively.

In an embodiment, the display assembly further comprises a movable member which is rotationally coupled to the indication member. The movable member is further coupled to the display member and rotatable with respect to the housing. As an advantage, a rotation of the movable member may be transferred to a rotation of the indication member with respect to the housing such that different pieces of information provided by the indication member may be indicated to a user, e.g. during setting of a dose of drug to be dispensed from the drug delivery device.

In an embodiment, the display assembly is configured such that, when the movable member is rotated with respect to the housing, the rotating movable member moves the display member axially with respect to the housing to display different indicia through the display member window. In this way, an indication of dose information may be displayed to the user of the display assembly and/or the drug delivery device in a way in which the user is not confused but can clearly identify said information through the display member window.

A further aspect relates to a drug delivery device comprising the display assembly. The drug delivery device further comprises a dose setting mechanism which is configured such that the indication member indicates a set dose of drug or a unit thereof and a drive mechanism to dispense a dose of drug. Preferably, the indication member indicates a dose or filling status of the drug delivery device, thereby also indicating the actual amount or quantity of a drug during dispensing, as well as an amount remaining to be dispensed if a dose dispensing operation of the drug delivery device is interrupted.

In an embodiment, the movable member is axially movable with respect to the housing and configured to interact with the dose setting mechanism of the drug delivery device such that, when a dose of drug is set, the movable member moves axially. This embodiment is particularly expedient, as during setting of a dose of drug, a component of the drug delivery device which is to be actuated by the user is usually moved proximally with respect to e.g. a housing component. Thus, it is advantageous to embody the movable member such that it also moves axially with respect to the housing, e.g. when a dose of drug is set, as, then, the state of the set dose is instantaneously displayable through the display member window such that a user can just identify, e.g. the dose or filling status, such as the amount of drug which is actually set or dispensed.

In an embodiment, the movable member is threadedly engaged with the housing. As an advantage of this embodiment, the axial distance by which the movable member is moved e.g. proximally with respect to the housing, as mentioned above, may be determined by the lead of said thread engagement.

In an embodiment, the movable member is threadedly engaged with the display member. According to this embodiment, e.g. during setting of a dose, wherein the movable member may be moved axially with respect to the housing, also the display member is moved axially with respect to the housing. According to the configuration of the thread engagement between the movable member and the display member, the display member may be moved axially, preferably in the proximal direction. Preferably, the thread engagement of the movable member and the housing and that of the movable member and the display member have a common sense of rotation such that the display member is moved in the same direction with respect to the housing when the movable member is moved in that direction with respect to the housing.

In an embodiment, the display assembly is configured such that an axial distance by which the display member is moved is greater than an axial distance by which the movable member is moved, when, during an operation of the display assembly, the movable member is moved axially with respect to the housing. According to this embodiment, more space for the display of dose information can be generated. Moreover, the axial extension or movement of the movable member can be minimised in order to improve the ergonomic design of the display assembly or the drug delivery device. Particularly, the axial length of the drug delivery device can be minimised while allowing for a comparatively large axial travel distance of the display member.

In an embodiment, the display member comprises an inner thread and the movable member comprises an outer thread. This is a preferred embodiment as the display member may preferably be configured sleeve-like such that it retains or accommodates further components of the drug delivery device. Accordingly, the movable member can be provided with an inner thread, preferably, such that said inner thread contributes to the threaded engagement of the movable member with the housing. Preferably, the movable member is further threadedly engaged to an inner housing component comprising an outer thread. The inner housing preferably forms the housing along with further components. The housing of the drive assembly may constitute a housing of the drug delivery device.

In an embodiment, the movable member is rotationally locked with respect to the indication member. This embodiment allows a configuration of the drive assembly, wherein, at any time when the movable member rotates with respect to the housing, such as during an operation of the drug delivery device, the indication member follows such that the indicia are instantaneously arranged such that e.g. indicia can be indicated to the user.

In an embodiment, the indication member is rotatable but axially constrained with respect to the housing. This embodiment allows for a compact design of the drug delivery device, particularly with respect to an axial extension of the drug delivery device.

In an embodiment, the display member comprises a colored section which is aligned with the display member window. The colored section is, preferably, arranged on a projection extending from a main body of the display member. Preferably, the colored section is, furthermore, axially aligned with the display member window. This allows for an indication of the colored section through a further component, such as a housing window of the display assembly or the drug delivery device which may partially retain the display member. The colored section is, preferably provisioned to provide for further dose information.

In an embodiment, the display member further comprises a further colored section which is axially aligned with the display member window on a side of the display member window which faces away from the colored section. The further colored section is, preferably, not arranged on the projection but, e.g., on a main body of the display member. The further colored section is, preferably provisioned to provide for further dose information.

The colored section and the further colored section may axially adjoin the display member window, respectively.

In a preferred embodiment, the projection extends axially offset, preferably distally offset from the display member window. According to this embodiment, a shape or external dimension of the display member may be adjusted to further components of the drug delivery device. For example, the projection may at least partly axially overlap with a cartridge of the drug delivery device when said device is assembled.

In an embodiment, the movable member and/or the indication member is at least partly received by the display member. Thereby, it is achieved that the display member may at least partly cover a section of the movable member and/or the indication member and, in this way, the colored section or the further colored section may be indicated to the user, e.g. through a housing window of the display assembly and the movable member and/or the indication member is not visible to, e.g. the user.

In an embodiment, the display assembly comprises a spring member which is coupled to the housing and to the indication member. According to this embodiment, it can be achieved that the display assembly is coupled to a mechanism, such as a return mechanism. The return mechanism may be configured to drive the display assembly during a dose dispensing operation, particularly to drive rotation of the indication member and the movable member and axial movement of the display member when a dose of drug is being dispensed from the device.

In an embodiment, the display assembly is configured such that, when a dose is set, the indication member is rotated from an initial position to a dose set position, thereby biasing the spring member. When a dose is dispensed, the spring member drives movement of the indication member towards the initial position of the indication member. Thereby, a functionality may be provided in which the display member is connectable to the dose setting mechanism and to a dose dispensing mechanism of the drug delivery device.

In an embodiment, the movable member is coupled to the dose dispensing mechanism of the drug delivery device.

In an embodiment, the display member comprises a minimum dose stop feature which is arranged and configured to interact with a complementary minimum stop feature such that axial movement of the display member in a first direction with respect to the housing is prevented when no dose is set. Thereby, the display member window is arranged in a start position. This embodiment addresses a safety aspect of the drug delivery device, wherein it may be prevented that, in an initial state of the drug delivery device, wherein no dose is set, negative doses are set.

In an embodiment, the indication member comprises the complementary minimum stop features which is configured and arranged to interact with the minimum dose stop features when the indication member is arranged in a first rotational end position with respect to the housing such that axial, preferably distal travel of the display member is prevented.

In an embodiment, the display member comprises a maximum dose stop feature which is arranged and configured to interact with a complementary maximum stop feature such that axial movement of the display member in a second direction with respect to the housing is prevented when a maximum settable dose of drug is set. Thereby, the display member window is arranged in an end position. According to this embodiment, the user is hindered from setting a further dose when the maximum settable dose of drug is already set by the drug delivery device and, in this way, safety of the device can be increased.

In an embodiment, the indication member comprises the complementary maximum stop features which is configured and arranged to interact with the maximum dose stop features when the indication member is arranged in a second rotational end position with respect to the housing such that axial, preferably proximal travel of the display member is prevented.

In an embodiment, the minimum dose stop feature and the minimum dose stop feature of the display member, circumferentially adjoin the display member window. According to this embodiment, the above mentioned functionality can be achieved most expediently.

Preferably, the first direction is opposite to the second direction. The first direction may relate to a movement of the display member towards a negative dose or, as the case may be, towards a decreased dose and the second direction, preferably, relates to a direction of movement of the display member towards an increased dose.

In an embodiment, the housing comprises a housing window. Expediently, the housing window is arranged and configured such that a user may identify dose information, particularly dose information provided by the indicia through the display member window. The display assembly is, preferably, configured such that the display member window is visible through the housing window.

In an embodiment, the display member is configured such that, during an operation of the display assembly, the display member window is moved within the limits of the housing window. According to this embodiment, it is advantageously achieved that, during an operation of the device, to reliably indicate dose information through the housing window, the display member window is visible through the housing window.

An operation of the drug delivery device may relate to the setting, as well as to the dispensing of a dose of drug from the device.

In an embodiment, the display member is configured opaque. Thereby, an effective masking of indicia of the indication member by the display member may be achieved such that only indicia which are provisioned and/or arranged to be displayed by the display member window, are displayed to the user.

In an embodiment, the display assembly is configured such, that when a dose is set, the colored section or the further colored section is at least partly visible through the housing window. This embodiment enables a user to identify further dose information, such as a further visual hint of an actual dosing status of the device to the user via the colored section through the housing window.

In an embodiment, the housing is transparent. The housing window may be formed by an opaque covering of the housing.

In an embodiment, the drug delivery device comprises a needle or a needle assembly. Through said needle or needle assembly, a drug or medical substance which may be retained in the cartridge, can be dispensed from the drug delivery device.

The term “drug” or “medical substance”, as used herein, preferably means a pharmaceutical formulation containing at least one pharmaceutically active compound, wherein in one embodiment the pharmaceutically active compound has a molecular weight up to 1500 Da and/or is a peptide, a protein, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin. Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39), wherein the group -Lys6-NH2 may be bound to the C-terminus of the Exendin-4 derivative;

or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5-des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2, H-Asn-(Glu)5-des Pro36, Pro37, Pro38 [Trp(O2)25, Asp28] Exendin-4(1-39)-(Lys)6-NH2, H-(Lys)6-des Pro36 [Met(O)14, Asp28] Exendin-4(1-39)-Lys6-NH2, des Met(O)14 Asp28 Pro36, Pro37, Pro38 Exendin-4(1-39)-NH2, H-(Lys)6-desPro36, Pro37, Pro38 [Met(O)14, Asp28] Exendin-4(1-39)-NH2, H-Asn-(Glu)5-des Pro36, Pro37, Pro38 [Met(O)14, Asp28] Exendin-4(1-39)-NH2, des Pro36, Pro37, Pro38 [Met(O)14, Asp28] Exendin-4(1-39)-(Lys)6-NH2, H-(Lys)6-des Pro36, Pro37, Pro38 [Met(O)14, Asp28] Exendin-4(1-39)-(Lys)6-NH2, H-Asn-(Glu)5 des Pro36, Pro37, Pro38 [Met(O)14, Asp28] Exendin-4(1-39)-(Lys)6-NH2, H-Lys6-des Pro36 [Met(O)14, Trp(O2)25, Asp28] Exendin-4(1-39)-Lys6-NH2, H-des Asp28 Pro36, Pro37, Pro38 [Met(O)14, Trp(O2)25] Exendin-4(1-39)-NH2, H-(Lys)6-des Pro36, Pro37, Pro38 [Met(O)14, Asp28] Exendin-4(1-39)-NH2, H-Asn-(Glu)5-des Pro36, Pro37, Pro38 [Met(O)14, Trp(O2) 25, Asp28] Exendin-4(1-39)-NH2, des Pro36, Pro37, Pro38 [Met(O)14, Trp(O2)25, Asp28] Exendin-4(1-39)-(Lys)6-NH2, H-(Lys)6-des Pro36, Pro37, Pro38 [Met(O)14, Trp(O2)25, Asp28] Exendin-4(S1-39)-(Lys)6-NH2, H-Asn-(Glu)5-des Pro36, Pro37, Pro38 [Met(O)14, Trp(O2) 25, Asp28] Exendin-4(1-39)-(Lys)6-NH2;

or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a “Y”-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a “sandwich” shape, held together by interactions between conserved cysteines and other charged amino acids.

There are five types of mammalian Ig heavy chain denoted by α, δ, ϵ, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ϵ have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ϵ have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An “antibody fragment” contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

Features which are described herein above and below in conjunction with different aspects or embodiments, may also apply for other aspects and embodiments. Further features and advantageous of the subject matter of the disclosure will become apparent from the following description of the exemplary embodiment in conjunction with the figures, in which.

Figure 7A:
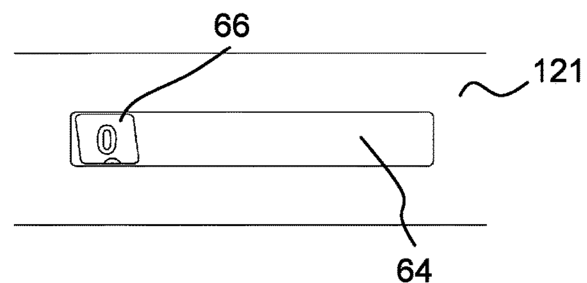
Figure 7B:
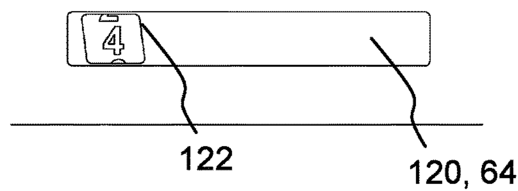
Figure 7C:
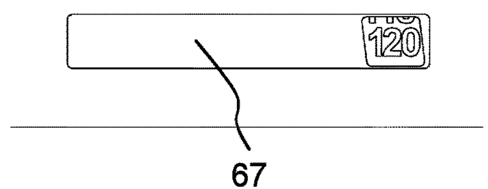

FIGS. 7A-C illustrate different states of a display assembly of the drug delivery device, respectively.

Figure 8:
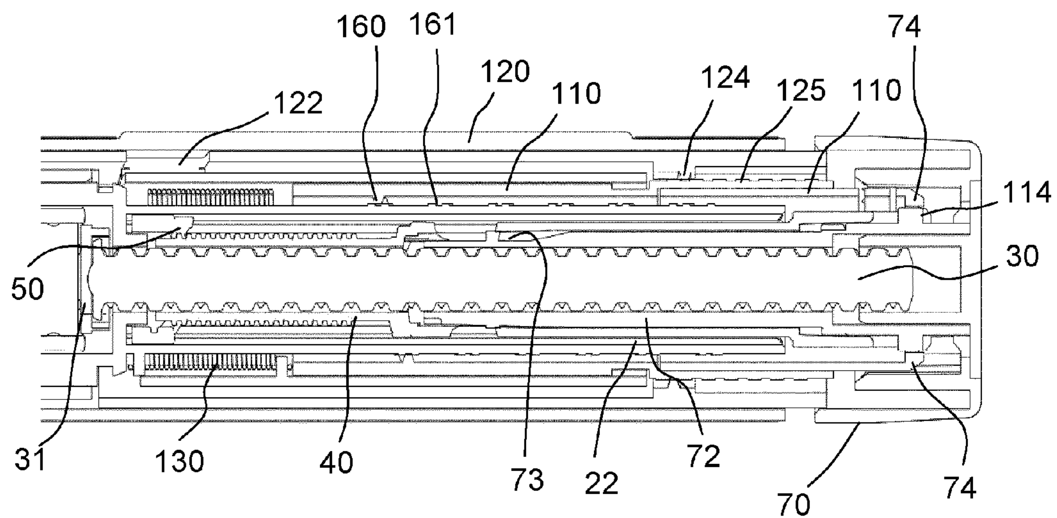

FIG. 8 shows a partial longitudinal section view of components of the drive mechanism of the drug delivery device.

Figure 9:
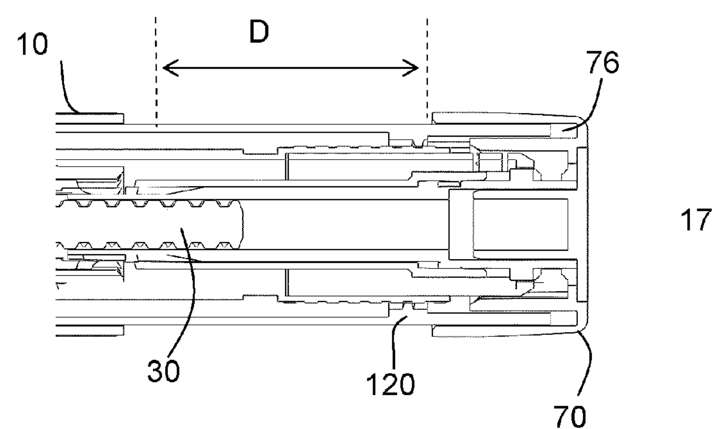

FIG. 9 shows a partial longitudinal section view of inner components of the drug delivery device.

Figure 10:
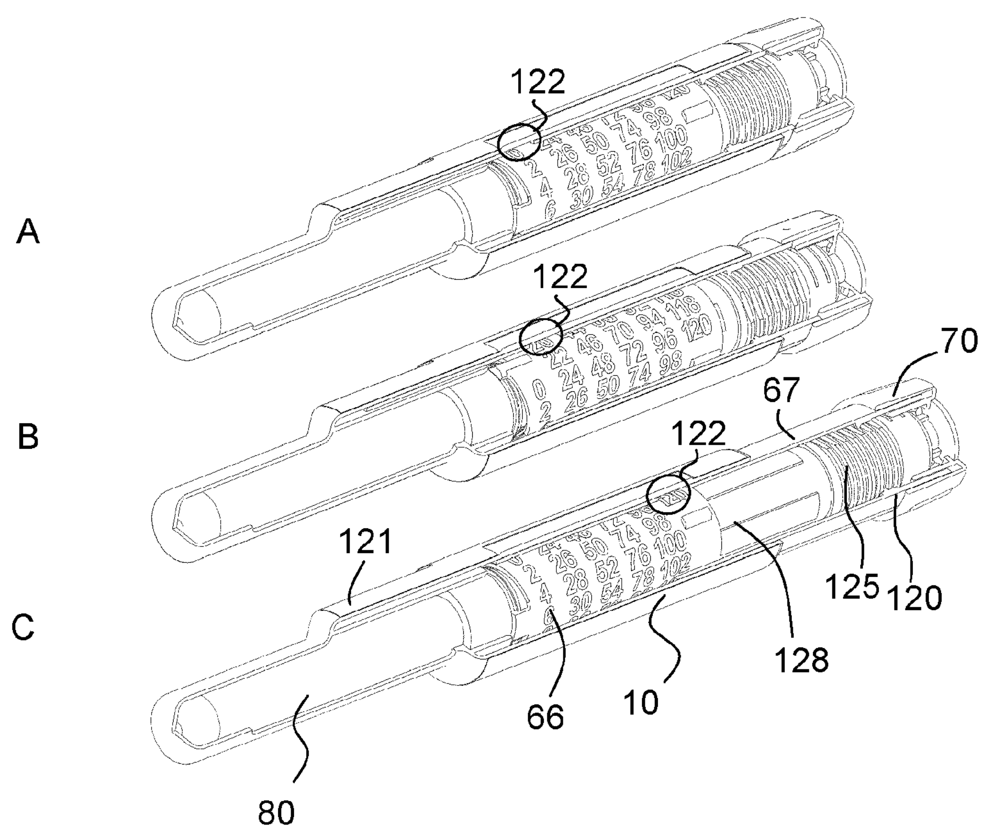

FIGS. 10A-C show a perspective view of components of a drug delivery device, respectively, wherein different states of the drug delivery device are depicted.

Figure 11:
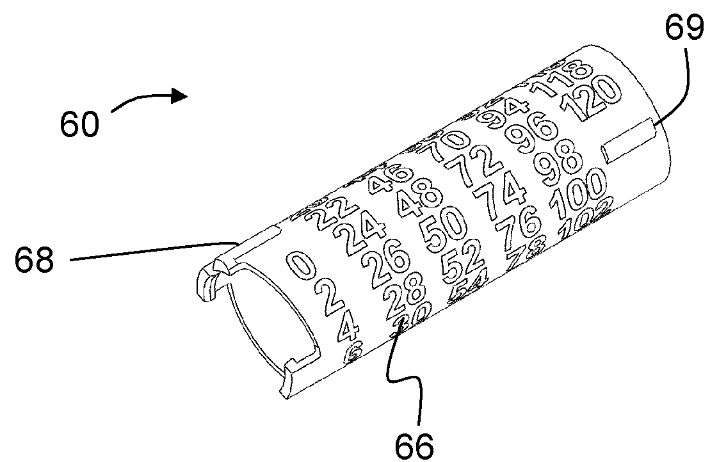

FIG. 11 shows a perspective view of an indication member of the drug delivery device.

Figure 12:
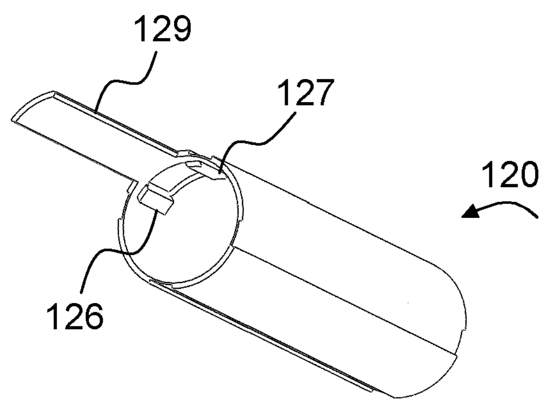

FIG. 12 shows a perspective view of a display member of the drug delivery device.

FIGS. 13A-C show a partial perspective view of components of the drug delivery device, respectively.

Figure 14:
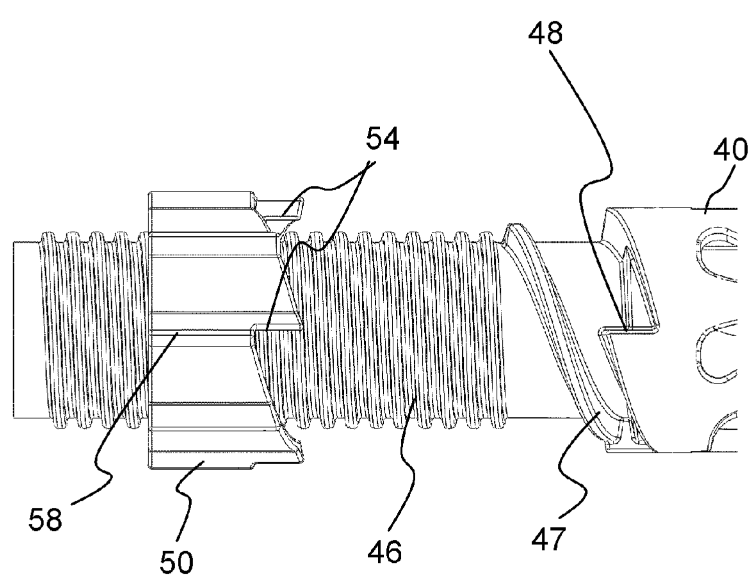

FIG. 14 shows a side view of a last dose member and parts of a drive member of the drug delivery device.

Figure 15:
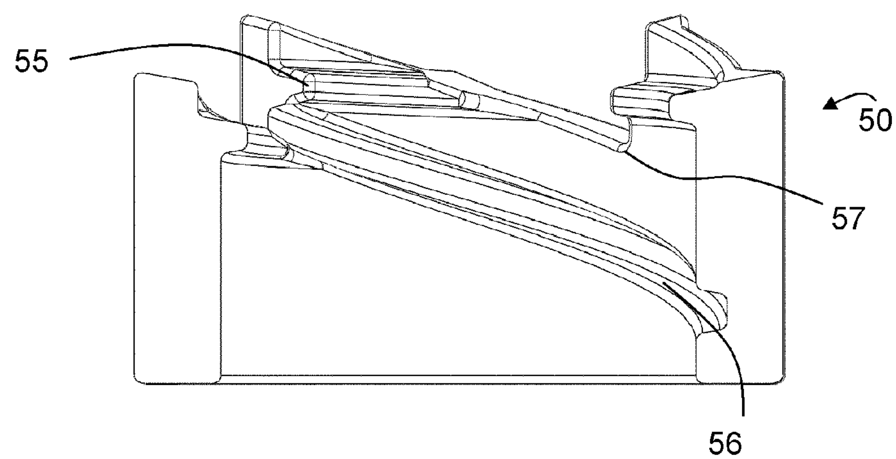

FIG. 15 shows a longitudinal section view of the last dose member of the drug delivery device.

Like elements, elements of the same kind and identically acting elements may be provided with the same reference numerals in the figures. Additionally, the figures may be not true to scale. Rather, certain features may be depicted in an exaggerated fashion for better illustration of important principles.

Figure 1:
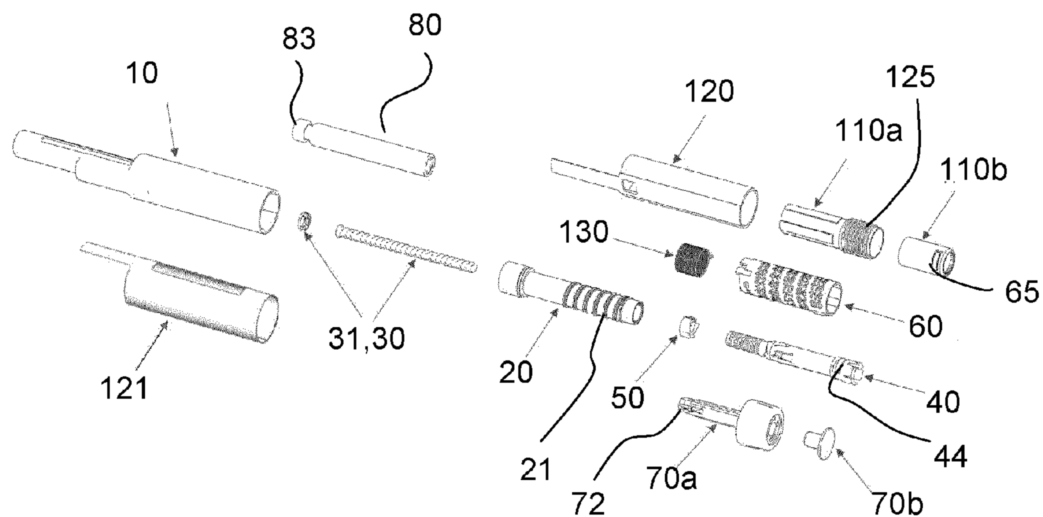
FIG. 1 shows an exploded view of components of a drug delivery device.

As shown in FIG. 1, the drug delivery device comprises a housing 10. The housing 10 may constitute an outer body of the drug delivery device 100. The housing 10 comprises a longitudinal axis which may coincide with the longitudinal axis x (cf. FIG. 2) of the drug delivery device 100. The drug delivery device 100 further comprises a label 121 which may be affixed to an outer surface of the housing 10. The label 121 may comprise an aperture which may define a housing window 123 when the label 121 is affixed to the housing 10. In a preferred embodiment, the outer housing 10 is transparent. Preferably, the label 121 is opaque.

Figure 2:
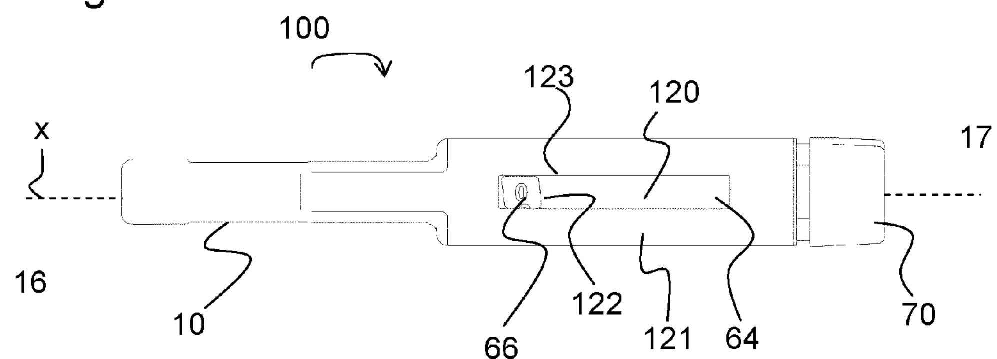
FIG. 2 shows a side view of the drug delivery device.

In FIG. 2, it is shown that the label 121 covers most of the housing 10 with the exception of the window 123. The outer housing part 10 is a generally tubular element having a distal part, which forms a cartridge holder for receiving cartridge 80, and a proximal part.

The drug delivery device 100 further comprises an inner body 20, a piston rod 30, a driver 40, a nut 50, an indication member 60 and a cartridge 80. The drug delivery device 100 may comprises additional components such as a needle arrangement comprising a needle hub and a needle cover.

The drug delivery device 100 further comprises a first button part 70*a* which, after an assembly of the drug delivery device 100, is preferably rigidly fixed to a second button part 70*b* in order to form a button 70 of the drug delivery device 100 (cf. in FIG. 1). When, in the following, it is referred to the button 70, it is referred to both components (70*a* and 70*b*) which are rigidly connected to each other. When referring to a dose member, it may also be referred to the button. As the same component is meant, the same reference numerals are used for the button and the dose member. The dose member may be the button.

The button 70 may have a surface allowing a user to easily grip the button 70.

The inner body 20 is a generally tubular element having different diameter regions. When referring to an inner housing, it may also be referred to the inner body. As the same component is meant, the same reference numerals are used for the inner body and the inner housing. The inner housing may be the inner body.

Figure 3:
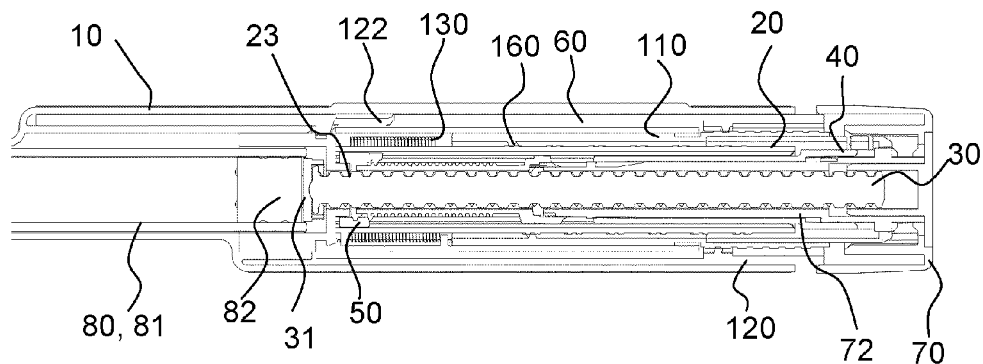
FIG. 3 shows a longitudinal section view of components of a drive mechanism of the drug delivery device.

As can be seen, e.g. in FIG. 3, the inner body 20 is received in the housing 10 and permanently fixed therein to prevent any relative movement of the inner body 20 with respect to the housing 10. An external thread 21 is provided on the outer surface of the inner body 20. Further, splines 22 are provided on the inner surface of the inner body 20 which are shown in FIG. 5, for example. As can be taken from FIGS. 3 and 4, the inner body 20 has near its distal end an inner thread 23.

The piston rod 30 is an elongate element having two external threads (not explicitly indicated) with opposite hand which overlap or interfuse each other. One of these threads engages the inner thread 23 of the inner body 20. The drug delivery device further comprises a bearing 31. As shown in FIG. 3, the bearing 31 may interact with the piston rod when the drug delivery device 100 is in an assembled state. The bearing 31 is separated from the piston rod 30 such that the bearing 31 remains seated on the distal end of the piston rod 30 to allow relative rotation between the bearing 31 and the piston rod 30.

The driver 40 is a generally tubular element having different diameter regions. When referring to a drive member, it may also be referred to the driver. As the same component is meant, the same reference numerals are used for the drive member and the driver. The drive member may be the driver. The driver 40 is rotationally locked to the button 70, e.g., via a corresponding spline engagement.

A distal region of the driver 40 has an external thread 46, as will be outlined below. An inner surface of the driver 40 has an inner thread (not explicitly indicated) engaging one of the external threads of the piston rod 30. The driver 40 surrounds the piston rod 30 and is at least partly located within inner body 20 when the device 100 is assembled (cf. FIG. 3). The driver 40 has a proximal opening which will be explained in more detail below. Further, a resilient finger 44 is provided on the driver 40 by a U-shaped cut in the skirt of the driver 40, as shown in FIG. 1. The finger 44 is allowed to flex in the axial direction and engages a button 70 (see below). In addition, a flexibly hinged protrusion 45 (cf. FIG. 8) is provided on the driver 40 by a similar cut-out in the skirt of the driver 40. The protrusion 45 may form or contribute to the function of a clutch feature. The protrusion 45 is allowed to flex radially inwardly. Protrusion 45 engages splines 22 of the inner body 20. The splines 22 may constitute a complementary clutch feature. The protrusion 45 and splines 22 additionally form a clicker arrangement that provides tactile and audible feedback to the user when setting or dialling doses. This clicker arrangement has the further functions of defining discrete positions for the indication member 60 when dialling and of providing a method of locking the rotation of the driver 40 and, hence, the dose member 70. This functionality may be provided by a releasable clutch mechanism being configured such that, in the setting mode of operation, the dose member 70 is rotatable with respect to the housing and, in the dispensing mode of operation, a clutch feature interacts with a complementary clutch feature such that the dose member 70 is rotationally locked with respect to the housing 10. During dialling, the button 70 is in an axial position relative to the driver 40 such that a pocket or recess 73 is located radially inwards of the protrusion 45. Thus, the protrusion 45 is allowed to flex radially inwards to overcome splines 22, thereby providing a tactile and audible feedback to the user.

The nut 50 is provided between the inner body 20 and the driver 40. When referring to a last dose member, it may also be referred to the nut. As the same component is meant, the same reference numerals are used for the last dose member and the nut. The last dose member may be the nut.

External ribs 58 of the nut 50 engage splines 22 of the inner housing 20. An internal thread 55 of the nut 50 engages the external thread 46 of the driver 40. Further, in the embodiment of FIG. 14, four rotational last dose stop features 54 are provided on nut 50 for interaction with corresponding drive member stop features 48 on the driver 40.

The indication member 60 is a generally tubular element. The indication member 60 is preferably rotatable but axially constrained with respect to the inner housing by corresponding stops. The indication member 60 is interposed between the inner body 20 and the housing 10. A series of indicia 66, such as numbers providing dose information, is provided, e.g. printed, on the outer surface of the indication member 60. The numbers are arranged on a helical line such that only one number or only a few numbers are visible through window 123 at a time.

A sleeve-like part 72 of the button 70 with a reduced diameter extends in the distal direction and is inserted into the driver 40 such that a limited relative axial movement is allowed but relative rotation is prevented. This is achieved by a corresponding feature on the sleeve-like part 72 which is guided in the proximal opening (not explicitly indicated) of the driver 40. A recess 73 which generally has the outline of the protrusion 45 is provided in the sleeve-like part 72 of button 70 (cf. FIG. 8).

The drug delivery device 100 further comprises a first movable member part 110*a* which, after an assembly of the drug delivery device 100, is preferably rigidly fixed to a second movable member part 110*b* in order to form a movable member 110 of the drug delivery device 100 (cf. in FIG. 1). When, in the following, it is referred to the movable member 110, it is referred to both components (110*a* and 110*b*) which are rigidly connected to each other. The movable member 110 has a sleeve-like shape with a longitudinal axis which, in an assembled state of the device, may coincide with the longitudinal axis x of the drug delivery device 100.

The two-component embodiment of the dose member 110 and the button 70 may, in collaboration with further components facilitate an easy assembly of the drug delivery device 100.

The drug delivery device 100 further comprises a display member 120. The display member 120 comprises a display member window 122. The movable member 110 may partly be received by the display member 120 when the drug delivery device 100 is assembled. The display member 120 is, preferably, rotationally locked with respect to the housing 10. The movable member 110 is at least partly received by the display member 120.

The drug delivery device 100 further comprises a spring member 130 (cf. FIG. 1). The spring member 130 is preferably connected to the inner housing 20 and the indication member 60. Alternatively, the spring member 130 may be connected to further components.

Figure 13:
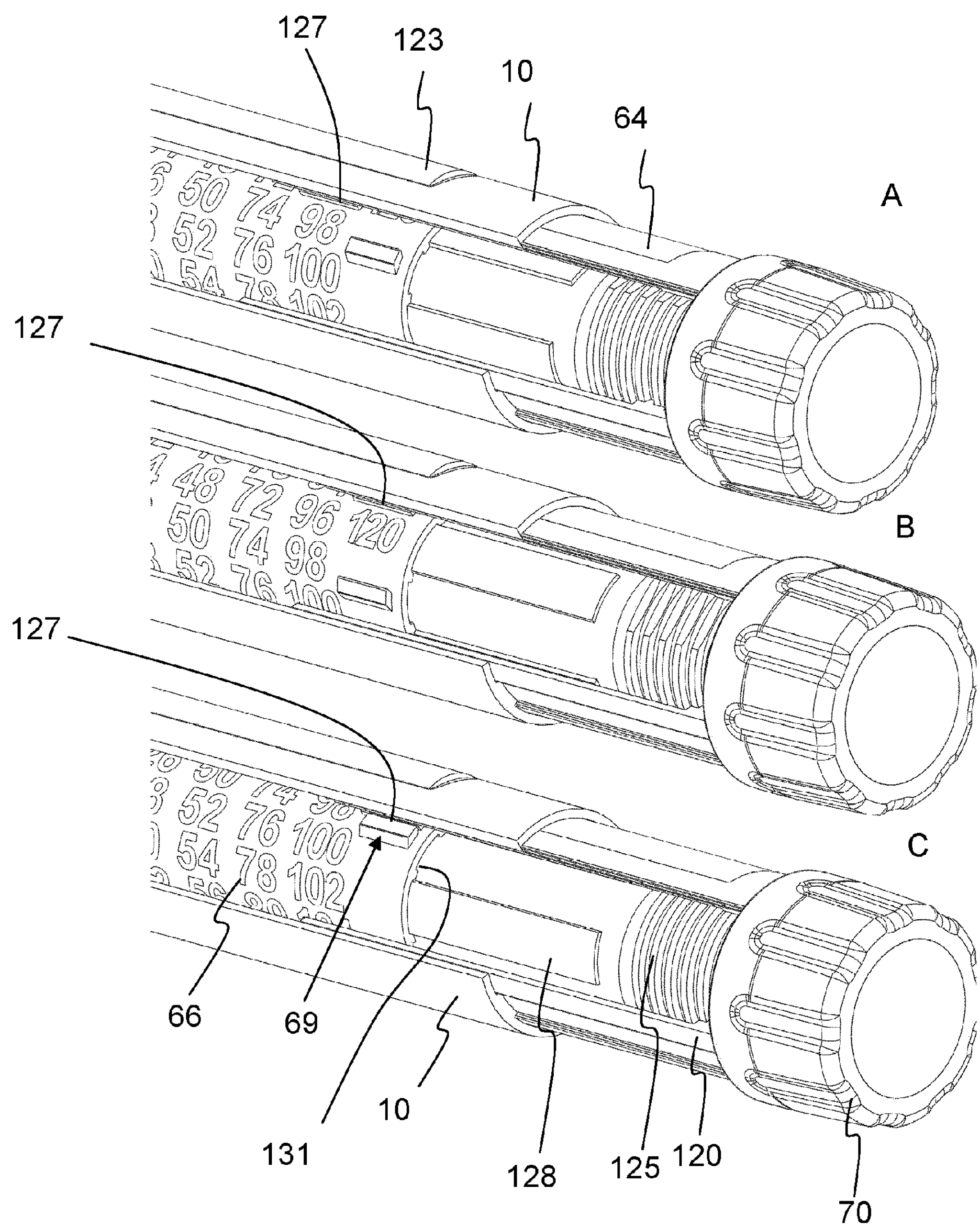

The movable member 110 is rotationally locked with respect to the indication member 60 via movable member splines 128 and indication member splines 131 (cf. FIG. 13). The movable member 110 is further threaded to the display member 120 via a movable member thread and a distal member thread (cf. 124, 125 in FIG. 8).

A releasable rotational locking mechanism is provided between the movable member 110 and the dose member 70 by corresponding locking teeth 114 and 74 (cf. FIG. 8). If teeth 74 of the button 70 engage locking teeth 114 of the movable member 110, the button 70 and the movable member 110 are rotationally locked. The resilient finger 44 of the driver 40 biases the button 70 in the proximal direction of the device 100, i.e. in a direction engaging the locking teeth 74, 114. In this situation, the drug delivery device is in a setting mode of operation, wherein the movable member 110 and the dose member 70 are rotationally locked.

The releasable rotational locking mechanism can be released, thereby allowing relative rotation by shifting the button 70 axially with respect to the housing 10 against the bias of finger 44, whereby the drug delivery device 100 is switched from the setting mode to a dispensing mode of operation.

Further, a dispense clicker is provided by flexible arms 65 on the movable member 110 and a toothed profile on the inner side of button 70.

FIG. 2 shows a drug delivery device 1 in the form of an injection pen. The device has a distal end 16 and a proximal end 17.

In FIG. 2, an indicium 66, particularly the number "0" is depicted by the drug delivery device 100 through the display member window 122 and the housing window 123. In FIG. 2, the drug delivery device is in an initial state, wherein no dose has been or yet been dispensed. The initial state may refer to an as-assembled state of the device. In this state, the moveable member 110, the display member 120 and the indication member 60 are preferably in an initial position. When a dose is set, said components are preferably in a dose set position.

In FIG. 2, the mentioned indicium 66 is shown at a distal end of the housing window 123. The display member window 122 is proximally confined by a colored section 64 of the display member 120. Said colored section may comprise a first color, such as, e.g. red color. A further colored section (not shown in FIG. 2; cf. 67 in FIG. 7C) may confine or adjoin the display member window 122 distally.

The drug delivery device 100 is preferably configured such that, for setting a dose, the user has to rotate the dose member 70 in a first direction with respect to the housing 10, wherein, the dose member 70 moves also proximally with respect to the housing 10. Preferably, the drug delivery device 100 is configured such that when a dose of drug is set, the display member window 122 travels proximally—originating from the position shown in FIG. 2—within the housing window 123. Unsetting or cancelling of a previously set dose may be carried out by the user in that the user rotates the dose member 70 in a second direction, opposite to the first direction, with respect to the housing 10. Preferably, any size of a dose of drug can be set and unset in predefined increments between zero and a predefined maximum dose.

The drug delivery device 100 may further be configured such that, In order to deliver a previously set dose, the user has to manually press or shift the dose member 70 distally with respect to the housing 10.

The drug delivery device 100 comprises a drive assembly further comprising a drive mechanism and a return mechanism. The drive mechanism may comprise or relate to the piston rod 30 and the drive member 40. The return mechanism may comprise or relate to the spring member 130.

The drug delivery device 100 further comprises a display assembly which may comprise or relate to the display member, the indication member and the movable member. The display assembly may further comprise a housing which may constitute the housing 10 of the drug delivery device 100.

FIG. 3 shows a partial longitudinal section of the drug delivery device 100 depicting components of the drive mechanism and the return mechanism (cf. also FIG. 8).

In FIG. 3, the drug delivery device 100 is in a state, wherein no dose has yet been set or dispensed and a bung or piston 82 retained in the cartridge 80 is arranged at the proximal-most end of the cartridge 80. The cartridge 80 includes a pre-filled, necked-down cartridge reservoir 81, which may be typically made of glass. A piercable rubber seal (not shown) is located at the other, distal, end. A crimped annular metal band 83 is used to hold the rubber seal in place. The cartridge 80 is provided within the housing 10 with piston rod 30 and bearing 31 abutting bung 82.

In FIG. 3, components of the device 100 are preferably at least partially concentrically arranged around the longitudinal axis x of the drug delivery device 100. The movable member 110 and also the indication member 120 are arranged in the initial position. Further, the last dose member 50 is in its distal-most position with respect to the drive member 40, indicating that no dose has yet been set and dispensed from the device by the user.

The indication member 60 is preferably axially constrained to the inner body 20 such that the indication member 60 preferably only rotates during an operation of the drug delivery device 100 without being axially moved. An operation of the device 100 may comprise setting and dispensing of a dose.

The spring member 130 is preferably a torsion spring. Preferably, the spring member 130 is comprised by the return mechanism.

Figure 4:
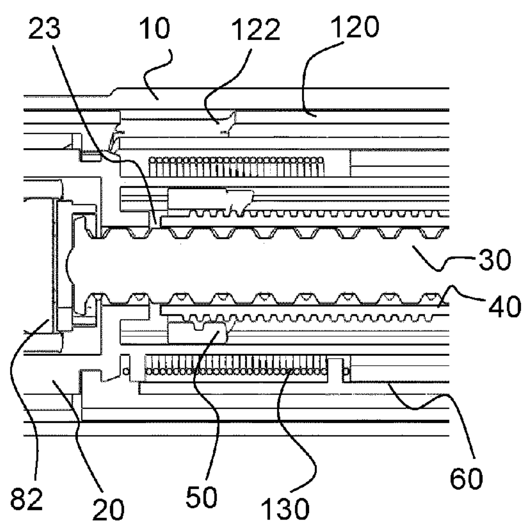
FIG. 4 shows a partial longitudinal section view of components of the drug delivery device.
Figure 5:
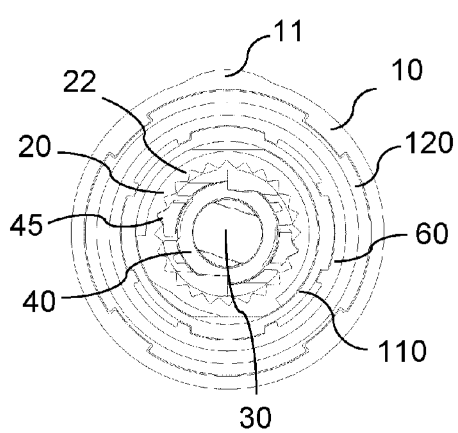
FIG. 5 shows a cross-sectional view of the drug delivery device.

FIG. 4 shows a section of the drug delivery device 100 of FIG. 3 in greater detail, thereby illustrating the location of the spring member 130. A distal end of the spring member 130 is connected to the inner housing 20 and a proximal end of the spring member 130 is connected to the indication member 60.

FIG. 5 shows a cross-sectional view of the drug delivery device 100. During setting of a dose, the dose member 70 is rotated along with the movable member 110, the drive member 40, and the indication member 60 in the first direction with respect to the housing 10. The movable member 110 is threaded to the inner housing 20 such that it also moves proximally with respect to the housing during setting of a dose. As the indication member 60 is rotated with respect to the housing, the spring member 130 is biased. Preferably, already in the initial state of the indication member 60, the spring member 130 is biased.

A torque of the spring member 130 must be overcome by the user when increasing the set dose. Said torque must be reacted by the splined interface (cf. splines 22 and protrusion 45) between the drive member 40 and the inner body 20 when the dose member 70 is rotated and a dose is set in the setting mode of operation. Said interface is arranged and configured such that the geometry of the splines 22 in the inner body 20 is biased to compensate for the nominal spring member torque such that torques relating to an increase of the set dose and a decrease of the set dose can be balanced or compensated, as the torque required to change the set dose is the sum of the torque to overcome the spring force of the spring member 130 which is positive when increasing the set dose and is negative when reducing the set dose, and the torque to overcome the splined interface.

Spline ramp angles of the splines 22 of the inner body 20 and the protrusion 45 on the drive member 40 are offset slightly to compensate for the effect of the spring torque of the spring member 130 during setting of a dose, such that the torque required to overcome the splined interface is greater when reducing the set dose than when increasing the set dose.

The splined interface between the splines 22 and the protrusion 45 may, alternatively, be configured symmetrical to provide the same overwinding torque when increasing or decreasing the set dose. Thereby, the spring member may be configured such that the torque may be considered small in comparison to typical user torques to change the set dose of drug delivery devices.

Figure 6:
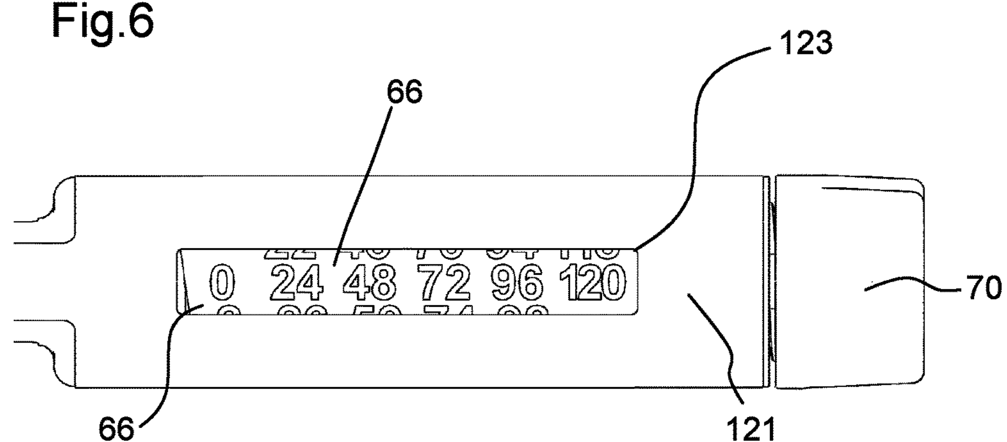
FIG. 6 shows a side view of components of a display assembly of the drug delivery device.

In FIG. 6, as compared to FIG. 2, the display member 120 is not shown such that indicia 66, particularly numbers indicating a quantity of drug, are displayed by the housing window 123. Next to the distal end of the housing window 123, "0" is indicated by the indication member 60 through the window 123. Next to the proximal end of the housing window 123, "120" is indicated by the indication member 60 through the window 123. The number "120" may relate to a maximum settable dose of the drug delivery device 100.

The housing window 123 may be lens-shaped such that indicia 66 which are visible through the housing window 123 are magnified. The housing 10 may be transparent. The housing window 123 may also be formed by a lens element (cf. 11 in FIG. 5) which may be unitarily formed by the housing 10 and which forms an elevated structure of the housing 10. The label 121 may be arranged and affixed to the housing 10 such that said lens element is arranged within the above mentioned aperture of the label 121.

The lens element 11 may axially extend over the full axial length of the indication member 60 in which indicia 66 are arranged, when the drug delivery device is assembled, as shown in FIG. 6. Preferably, the display member 120 is opaque such that indicia 66 not corresponding to the current dose indication of the drug delivery device are masked out by the display member and cannot be identified by the user.

FIGS. 7A-C show different states of a display assembly of the drug delivery device 100, respectively. Therein, the display member 120 is assembled to the device (as compared to FIG. 6) with the effect that only one indicium 66, preferably the indicium corresponding to the current dose set or dispensed, is visible to the user. The axial position of the display member window 122, which is visible through the housing window 123, provides a visual indication of the current dose status of the device to the user. The surface of the display member 120 may also provide further dose information of the drug delivery device 100.

In FIG. 7A, the indication member 60 and the display member 120 are in the initial position and a dose of zero units of drug is set, such that "0" is visible through the display member window 122. The display member window 122 is in a start position. The colored sections 64, is arranged proximally beside the display member window 122. The colored section 64 may comprise red color. The device 100 is preferably configured such that, when a dose is set, the display member window 122 travels proximally and, simultaneously, the indication member 60 rotates with respect to the housing 10 such that different indicia 66 are displayed through the display member window 122. It is shown in FIGS. 7A to C that, thereby, the numbers indicating dose quantities are increased.

In FIG. 7B, a dose corresponding to four units or quantities of drug is set and "4" is displayed through the display member window 122, which is moved slightly proximally with respect to the housing, as compared to FIG. 7A.

In FIG. 7C, the maximum settable dose of 120 units of drug is set. In this case, the display member window 122 is arranged at its proximal-most position with respect to the housing 10, i.e. an end position of the display member window 122. Additionally, a further colored section 67 is displayed through the housing window 123 proximally beside the display member window 122. The further colored section 67 may comprise green color.

FIG. 8 shows a partial longitudinal section view of inner components of the drug delivery device 100. Therein, components of a drive assembly, comprising a drive mechanism and a return mechanism are shown in greater detail, as compared to FIG. 3, for example. It is shown that the movable member 110 comprises a movable member thread 125 and the display member comprises a display member thread 124 matching to the movable member thread 125. The movable member 110 further comprises an inner thread 160 matching to an outer thread 161 of the inner housing 20. Preferably, the lead of the threads 160, 161 defines or determines the axial distance (cf. D in FIG. 9) by which the dose member is moved distally with respect to the housing during setting of a dose.

The protrusion 45 of the drive member 40 is further shown in FIG. 8. An axial movement of the display member 120 relative to the housing 10 is generated by a combination of the thread engagement between the movable member 110 and the inner body 20 (cf. threads 160, 161) and the thread interface between the display member 120 and the movable member 110 (cf. threads 124, 125). Thus, said thread engagements, preferably enable a greater axial movement of the display member 120 with respect to the housing 10 to be carried out during setting of a given dose, than a corresponding axial movement of the dose member 70 with respect to the housing 10.

To this effect, the total distance, the display member 120 travels axially for one rotation of the dose member 70 may be a summation of the helical pitches of the thread 124 and the thread 161.

In FIG. 9, a longitudinal section view of the proximal end 17 of the drug delivery device 100 is shown. The figure shows the drug delivery device 100, wherein a comparatively large dose of drug is set, as the dose member 70 has already moved significantly proximally with respect to the housing 10. As compared to, for example, FIG. 8, a proximal end section of the display member 120 is arranged in an inner section 76 of the dose member 70. As the axial travel distance of the display member 120 during setting of a dose is greater than that of the movable member 110, the display member 120 increasingly axially overlaps the dose member 70 when the set dose is increased. In other words, during setting of a dose, the display member 120 is moved into the inner section 76, although, both components, i.e. the display member 120 and the dose member 70 move proximally with respect to the housing 10. To this effect, the inner section 76 is provisioned, which provides an accommodation for the display member 120 for set large doses without increasing the total length of the drug delivery device 100.

FIGS. 10A-C show perspective views of the drug delivery device 100, respectively, wherein the indication member 60 is visible through the housing 10. It is shown in FIG. 10A that no dose is set, as "0" is visible through the display member window 123. In FIG. 10B, a dose of 20 units of drug is set. In FIG. 10C, a maximum number of 120 units is set. Although, in this embodiment, a number of 120 units corresponds to the maximum settable dose, the drug delivery device 100 may also be configured such that more or less units of drug may be set and dispensed from the drug delivery device 100.

FIG. 11 shows a perspective view of the indication member 60. Indicia 66 are helically arranged around an outer surface of the indication member 60. It is further shown that the indicia 66 span a range from zero units to 120 units of drug. The indication member 60 further comprises a minimum stop feature 68 and a maximum stop feature 69 which are arranged beside the indicium indicating "0" and the indicium indicating "120", respectively, thereby adjoining the helical path of the indicia 66.

FIG. 12 shows a perspective view of the display member 120. Circumferentially beside the indication member window 122, a minimum dose stop feature 126 is provided, preferably affixed. At a side of the window 122, which faces away from the minimum dose stop feature 126, a maximum dose stop feature 127 is provided, preferably affixed. The display member 120 further comprises a projection 129. An outer surface of the projection 129 preferably comprises the further colored section 67. Said projection 129 is axially aligned with the display member window 122 with respect to the longitudinal axis x.

The minimum dose stop feature 126 is arranged and configured to interact with a minimum stop feature 68 such that axial movement of the display member 120 in a first axial direction with respect to the housing 10 is prevented when no dose is set. Thereby, the display member window 123 is arranged in a start position.

The maximum dose stop feature 127 is arranged and configured to interact with the maximum stop feature 69 such that axial movement of the display member 120 in a second axial direction, opposite to the first axial direction with respect to the housing 10 is prevented when a maximum settable dose of drug is set. Thereby, the display member window 123 is arranged in an end position.

The minimum dose feature 126 interacts with, preferably abuts the minimum stop feature 68 when no dose is set or when the user attempts to decrease the dose in this state. The maximum dose feature 127 interacts with, preferably abuts the maximum stop feature 69 when the maximum settable dose is set or when the user attempts to further increase the dose in this state. Said interactions may be illustrated in FIG. 13.

The relative position of said stop features (68, 69, 126, 127) limits the rotation of the indication member 60, as well as an axial movement of the display member 120 during a dose setting and/or dose dispensing operation. Said stop features (68, 69, 126, 127) may be formed by a protruding boss or shoulder protruding from a main body of the indication member 60 and the display member 120, respectively. Said stop features are arranged and configured such that the dose settable by the drug delivery device 100 is restricted to the range of indicia 66 on the display member 60 which corresponds to the range of settable doses.

In dose positions between zero and the maximum settable dose, the stop features 68, 69 pass under the display member 120 in sections of the length of the indication member 120, where no stop features are provided.

By embodying said stop features (68, 69, 126, 127) such that the display members 120 and the indication member 60 directly interact, an alignment of the indicia 66 to be displayed by the display assembly can be easily controlled.

Abutment radii of the indication member 60 and the display member 120 are, preferably, large such that reaction forces are low.

An abutment length can be maximised, as an axial travel of the display member 120 during an operation of the drug delivery device 100 is large.

FIGS. 13A-C further illustrate the mentioned stop functionality between the indication member 60 and the display member 120. In FIG. 13A, a dose of 99 units of drug (not explicitly indicated) may be displayed to the user. In FIG. 13B, a dose of 119 units of drug (not explicitly indicated) may be displayed to the user. In FIG. 13C, a maximum settable dose of 120 units of drug (not explicitly indicated) may be displayed to the user. Here, the maximum indication stop feature 69 abuts with the maximum display stop feature 127.

In FIG. 14, the last dose member 50 and a distal section of the drive member 40 is shown in a side view. The last dose member 50 comprises last dose stop features 54. The last dose stop features 54 are configured to interact with drive member stop features 48 of the drive member 40. The last dose member 50 is threaded to a distal end of the drive member 40. Therefore, the drive member 40 comprises a first outer thread 46. The drive member 40 further comprises a second outer thread 47. The last dose member 50 comprises a proximal inner thread 55 matching to the first thread 46 (cf. FIG. 15). Moreover, the last dose member 50 comprises a distal inner thread 56 matching to the second thread 47 (cf. FIG. 15). The lead of the second thread is greater than the lead of the first thread 46. The root diameter of the first thread 46 and the second thread 47 is, preferably, equal. The outer diameter of the second thread 47 is, preferably, greater than the first thread 46. The first and/or the second thread 46, 47 are, preferably, single start threads.

The last dose member is operable to be moved from a start position to an end position when, during an operation of the device 100, doses of drug are subsequently set and dispensed. The start position may relate to an arrangement of the last dose member 50 at a distal end of the drive member 40. The end position may relate to a position of the last dose member 50, wherein the last dose stop features 54 rotationally abut the drive member stop features 48, thus forming a rotational stop such that a further increase of the set dose is prevented.

The last dose member 50 is furthermore rotationally locked but axially movable with respect to the inner housing 20 (not shown in FIG. 14). To this effect, the last dose member 50 comprises ribs 58 which are axially guided by the housing splines 22 when the drive member 40 is rotated with respect to the housing 10.

Preferably, an axial extension of the dose stop feature is greater than a pitch or lead of the first thread section and less than a pitch of the second thread section. In FIG. 14, only half of a turn of the second thread is shown. Nevertheless, a pitch of the second thread may be determined by the double axial extension of the second thread 47, as shown in FIG. 14.

FIG. 15 shows a longitudinal section view of the last dose member 50. The last dose member 50 comprises a recess 57. The pitch of the distal thread 55 may be 0.7 mm and the pitch of the proximal thread 56 may be 6 mm. According to this embodiment, the overall device length of the drug delivery device 100 may be reduced by 6.5 mm, assuming a cartridge capacity of 450 units of drug. The mentioned numbers or values are not restrictive. Particularly, the length reduction of the device results from the first thread 46 being configured as a single start thread.

According to the provision of the first and the second thread, as mentioned, the stop features 48 and 54 can be embodied larger, i.e. with a longer axial extension. Thereby, stability of the last dose member 50 can be increased. This is due to the fact that, as the pitch is increased, when the last dose member 50 is moved proximally with respect to the drive member 40, said stop features can be embodied more robust. As the last dose member 50 moves proximally with respect to the drive member 40, e.g. during setting of a dose, at a certain point, the last dose member disengages from the first thread 46 and engages to the second thread 47.

The lead of the first thread 46 controls the axial travel of the last dose member 50 for the majority of the required rotation of the drive member 40, which occurs during dose setting only. Preferably, the second thread 47 controls the axial travel of the last dose member 50 for the final 180° of rotation of the drive member 40 during setting of a dose. Said embodiment of the two different threads allows to increase the size and strength of the stop features 48 and 54 such that stability is maintained. When the set dose corresponds to the amount of medicament remaining within the cartridge, the dose member stop features 54, preferably, abut the drive member stop features 48 such that a user is prevented from setting a greater dose.

As an alternative to the mentioned embodiment, the drive member 40 may also comprise only a single fine pitch thread (cf. first thread 46) in lieu of the mentioned first and second thread. This embodiment allows for a significant reduction of the axial space required for the movement of the last dose member 50 during an operation of the drug delivery device 100. This reduction enables a shorter overall device length or facilitates the accommodation of larger capacity drug cartridges.

During dispensing of a dose, the energy required to overcome the friction involved or caused by the movements of the indication member 60, the movable member 110 and the display member 120 is, preferably, expended by the return mechanism, particularly by the biased drive spring. Still further, the friction originating from a dispense clicker mechanism, as mentioned above, is provided by the return mechanism. During dose dispensing, the dispense clicker mechanism is active which involves button 70 and the movable member 110. The dispense clicker mechanism provides primarily audible feedback to the user that drug is being dispensed. The interaction between the flexible arms 65 on the movable member 110 and the toothed profile on the button 70 provides this dispense click. Relative rotation is only allowed in one direction. This occurs when the movable member 110 and the button 70 are decoupled during dispense and a click is produced for every unit of drug.

The torque exerted by the spring member 130 or required to bias the spring member 130 is preferably low, namely in the range of 0.5 to 2 Nmm. Said torque is required at the zero dose position and, as the spring member 130 is wound during setting of a dose, the torque increases to a maximum torque of e.g. 5 Nmm. The torque exerted by the spring member 130 is preferably chosen such that it has minimal impact on the setting torques the user has to expand during e.g. setting of a dose of drug.

By the provision of the return mechanism, the helical pitch of a threaded interface between the inner body 20 and the movable member 110 (threads 160, 161) can be reduced by 35%, as compared to a comparable embodiment in which no return mechanism is provisioned. To this effect, the axial travel of the movable member 110 for a given dose position or to set a given dose is reduced by 35%, as well.

When the axial travel of a movable member 110 is reduced as mentioned, the axial pitch between adjacent indicia 66 may reduce to approximately 4.3 mm which is considered insufficient for an easily readable state of the art display assembly, particularly for large set doses, which may require three digits, i.e. more than 100 units of drug. Therefore, the present disclosure provisions the functionality mentioned above relating to the inner section 76 of the dose member 70, wherein, during setting of a dose, the inner section accommodates a proximal end of the display member 120.

Reduction of the helical pitch of the threads 160, 161 is facilitated by the return mechanism mentioned above, as no portion of the axial force applied by the user during dispensing of a dose needs to be used to return the display member 110, the indication member 60 and the movable member 110 during dispensing of a dose. A torque must be applied to return, i.e. rotate, the indication member 60 and the movable member 110. In existing devices, without a return mechanism, this torque is generated by a portion of the axial force applied by the user overhauling or overcoming the threaded interface 160,161. To overcome said interface, its lead angle must be sufficiently large to overcome frictional forces. This limits the scope to reduce the pitch of the threaded interface, particularly considering the susceptibility of the device to friction at this threaded interface.

With the given drive assembly, including the return mechanism, the drive mechanism is therefore significantly less susceptible or dependent to frictional losses at the threaded interfaces.

By reducing the axial travel of the movable member 110, also an ergonomic operation or design of the drug delivery device 100 is improved, particularly for large doses set or users with restricted digit motions. Reducing said axial travel distance (cf. D in FIG. 2) of the movable member 110, e.g. when a maximum dose of drug is set, also enables a reduction of the length of the piston rod 30 and the inner body 20 which, in turn, enables a shorter overall device length.

The torque provided by the spring member 130 during dispensing of a dose is particularly sufficient to rotate and/or return the movable member 110 via the indication member 60 and, thereby, to return and/or distally move the display member 120. It is also sufficient to overcome the dispense clicker provided between the movable member 110 and the dose member 70. Any remaining torque is applied to the threaded interface between the movable member 110 and the inner housing 20, which generates a small axial force at the axial coupling between the movable member 110 and the drive member 40. Therefore the spring member 130 may provide a small axial assistance force to the drive member 40 when a dose of drug is dispensed.

To use the device 100, a user has to select a dose by a rotation of the dose member 70 in the first direction. Due to the threaded engagement between the movable member 110 and the inner housing 20, the dose member 70 winds out of the device 100, as, in the setting mode of operation, the dose member 70 is rotationally locked with respect to the movable member 110. Additionally, the number of units is incrementally counted and displayed through the display member window 123 which also moves proximally with respect to the housing. Rotation of the button 70 in the first direction causes the driver 40 to rotate and in doing so it advances along the piston rod 30 which remains fixed throughout dialling. At the maximum settable dose, the stop features 69, 127 shown in FIGS. 11 and 12 abut to prevent further increasing the dose.

The last dose member or nut 50 provides the function of counting the total number of dispensed units. The nut 50 locks the device 100 at the end of life and as such no greater doses of drug can be dialled or set. The last dose nut 50 and the driver 40 are threadedly engaged with respect to each other, as explained above. Further, the last dose nut 50 is assembled into splines 22 as shown in FIG. 8 such that the nut 50 and the inner body 20 are rotationally locked together (at all times). Rotation of the indication member 60 via a rotation of the dose member during dialling biases the spring member 130. Further, the rotation of the piston rod causes the nut 50 to advance along the driver 40. The nut 50 is free to slide axially within the inner body 20 at all times which allows advancement of the nut 50. The change in threads (cf. 46, 47, 55, 56) shown in FIGS. 14 and 15 towards the final doses axially accelerates the advancement of the nut 50 towards the end of life lockout condition. At the end of life condition, the stop features 54 of the last dose nut 50 contact the corresponding features 48 on the driver 40. The splined contact with inner body 20 reacts any torque transmitted by these stop features 48.

With the desired dose dialled, the device 100 is ready for dose dispensing. This basically requires pushing button 70 distally which will result in a disengagement of the clutch or locking teeth 74, 114. As mentioned above, when dialling a dose, the button 70 is 'biased out' and the locking teeth 74, 114 which rotationally lock the movable member 110 to the button 70 are engaged. Upon pressing the button 70, the locking teeth 74, 114 disengage and relative rotation between the movable member 110 and the button 70 is possible (cf. FIGS. 3 and 8). In all conditions, the driver 40 and the button 70 are rotationally locked together by engagement. At the same time, the relative axial movement of the button 70 with respect to the driver 40 results in the pocket or recess 73 being shifted relative to the protrusion 45. Thus, the protrusion 45 is prevented from flexing inwards because the protrusion 45 rests on a non-recessed area (cf. recess 73) of button 70. In this condition, the driver 40 and the button 70 are rotationally constrained to the inner body 20, thus preventing any rotation relative to the housing 10.

With the desired dose dialled the button 70 can be depressed manually by the user to drive the drive mechanism to dispense a dose and the piston rod 30 is driven forward to dispense drug from the cartridge 80. Thereby, the driving force applied by the user is transferred to the piston rod via the drive mechanism to drive the piston rod 30 in the distal direction with respect to the housing 10.

The interaction of mating threads between the piston rod 30, driver 40 and the movable member 110 and the inner housing 20 may deliver a mechanical advantage of 2:1 or 3:1.

When the button 70 has been pressed and the device is in the dispensing mode of operation, the energy of the biased spring member 130 is used to drives the return mechanism, wherein the movable member 110 is rotated back in the second direction towards its initial position with respect to the housing. The above mentioned dispense clicker mechanism is also driven by the spring member 130. Particularly, the spring member 130 rotates the indication member 60 in the second direction towards its initial position with respect to the housing, wherein the indication member 60 is rotationally locked to the movable member via the splines 128, 131. As the display member 120 is threaded to the movable member 110, also the display member window 123 is axially returned or moved back, thereby instantaneously indicating the actual dose information during the dispensing operation.

Preferably, the spring force of the spring member 130 is smaller than the driving force required to operate the device in the dispensing mode of operation such that a dose of drug is dispensed.

In the presented concept of the drug delivery device 100, though not being explicitly described, also mechanisms may be applied with eliminate the necessity of a priming of the drug delivery device 100.

The scope of protection is not limited to the examples given herein above. The invention is embodied in each novel characteristic and each combination of characteristics, which particularly includes every combination of any features which are stated in the claims, even if this feature or this combination of features is not explicitly stated in the claims or in the examples.

REFERENCE NUMERALS

10 Housing
11 Lens element
16 Distal end
17 Proximal end
20 Inner housing, inner body
22 Spline (inner body)
23 Inner thread (inner body)
30 Piston rod
31 Bearing
40 Drive member, driver
44 Resilient finger
45 Protrusion
46 First thread (dose member)
47 Second thread (dose member)
48 Drive member stop feature
50 Nut, last dose member
54 Last dose stop feature
55 Proximal thread (last dose member)
56 Distal thread (last dose member)
57 Recess (last dose member)
58 Rib (last dose member)
60 Indication member
64 Colored section
65 Flexible arm
66 Indicium
67 Further colored section
68 Minimum stop feature (indication member)
69 Maximum stop feature (indication member)
70 Dose member, button
72 Sleeve-like part
73 Recess (dose member)
74 Locking tooth (dose member)
76 Inner section
80 Cartridge
81 Cartridge reservoir
82 Piston, bung
83 Metal band
100 Drug delivery device
110 Movable member
114 Locking tooth (movable member)
120 Display member
121 Label
122 Display member window
123 Housing window
124 Display member thread
125 Movable member thread
126 Minimum dose stop feature
127 Maximum dose stop feature
128 Movable member spline
129 Projection
130 Spring member
131 Indication member spline
160 Inner thread (movable member)
161 Outer thread (inner body)
X Longitudinal axis
D Axial distance

The invention claimed is:

1. A display assembly for a drug delivery device, the display assembly comprising:

a housing having a proximal end, a distal end and a longitudinal axis;

a display member defining a display member window, the display member being rotationally locked to and movable with respect to the housing along the longitudinal axis (x);

an indication member comprising indicia; and a movable member which is rotationally coupled to the indication member, the movable member being further coupled to the display member and rotatable with respect to the housing, wherein, when the movable member rotates with respect to the housing, the rotating movable member moves the display member axially with respect to the housing to display different indicia through the display member window, wherein the movable member comprises a movable member thread and the display member comprises a display member thread and wherein the movable member thread is threadedly engaged with the display member thread.

2. The display assembly of claim 1, wherein the movable member is axially movable with respect to the housing and configured to interact with a dose setting mechanism of the drug delivery device such that, when a dose of drug is set, the movable member moves axially.

3. The display assembly of claim 1, wherein the movable member is threadedly engaged with an inner housing.

4. The display assembly of claim 1, wherein an axial distance by which the display member is moved is greater than an axial distance by which the movable member is moved, when, during an operation of the display assembly, the movable member is moved axially with respect to the housing.

5. The display assembly of claim 1, wherein the display member comprises an inner thread and the movable member comprises an outer thread.

6. The assembly of claim 1, wherein the movable member is rotationally locked with respect to the indication member.

7. The display assembly of claim 1, wherein the indication member is rotatable and axially constrained with respect to the housing.

8. The display assembly of claim 1, wherein the display member comprises a colored section which is aligned with the display member window.

9. The display assembly of claim 8, wherein the housing comprises a housing window, and wherein the display assembly is configured such that, during an operation of the display assembly, the display member window is moved within the limits of the housing window, wherein, when a dose is set, the colored section is at least partly visible through the housing window.

10. The display assembly of claim 1, wherein the movable member is at least partially received by the display member.

11. The display assembly of claim 1, comprising a spring member which is coupled to the housing and to the indication member, wherein, when a dose is set, the indication member is rotated from an initial position to a dose set position, thereby biasing the spring member and, when a dose is dispensed, the spring member drives movement of the indication member towards the initial position of the indication member.

12. The display assembly of claim 1, wherein the display member comprises a minimum dose stop feature which is arranged and configured to interact with a complementary minimum stop feature such that axial movement of the display member in a first direction with respect to the housing is prevented when no dose is set, the display member window thereby being arranged in a start position.

13. The display assembly according to claim 12, wherein the display member comprises a maximum dose stop feature which is arranged and configured to interact with a complementary maximum stop feature such that axial movement of the display member in a second direction, opposite to the first direction with respect to the housing is prevented when a maximum settable dose of drug is set, the display member window thereby being arranged in an end position.

14. A drug delivery device comprising:

a housing having a proximal end, a distal end and a longitudinal axis; and a display assembly comprising:

a display member attached to the housing, the display member defining a display member window, the display member being rotationally locked to and movable with respect to the housing along the longitudinal axis (x);

an indication member comprising indicia; and a movable member which is rotationally coupled to the indication member, the movable member being further coupled to the display member and rotatable with respect to the housing, wherein, when the movable member rotates with respect to the housing, the rotating movable member moves the display member axially with respect to the housing to display different indicia through the display member window, wherein the movable member is axially movable with respect to the housing and configured to interact with a dose setting mechanism of the drug delivery device such that, when a dose of drug is set, the movable member moves axially, wherein the movable member comprises a movable member thread and the display member comprises a display member thread and wherein the movable member thread is threadedly engaged with the display member thread.

15. The device of claim 14, wherein the moveable member is threadedly engaged with an inner housing.

16. The device of claim 14, wherein an axial distance by which the display member is moved is greater than an axial distance by which the movable member is moved, when, during an operation of the display assembly, the movable member is moved axially with respect to the housing.

17. The device of claim 14, wherein the display member comprises an inner thread and the movable member comprises an outer thread, wherein the movable member is rotationally locked with respect to the indication member, and wherein the indication member is rotatable and axially constrained with respect to the housing.

18. The device of claim 14, wherein the display member comprises a minimum dose stop feature which is arranged and configured to interact with a complementary minimum stop feature such that axial movement of the display member in a first direction with respect to the housing is prevented when no dose is set, the display member window thereby being arranged in a start position, and wherein the display member comprises a maximum dose stop feature which is arranged and configured to interact with a complementary maximum stop feature such that axial movement of the display member in a second direction, opposite to the first direction with respect to the housing is prevented when a maximum settable dose of drug is set, the display member window thereby being arranged in an end position.

* * * * *